(12) United States Patent
Shibuya et al.

(10) Patent No.: US 10,600,056 B2
(45) Date of Patent: *Mar. 24, 2020

(54) MOTION ANALYSIS DEVICE, MOTION ANALYSIS SYSTEM, MOTION ANALYSIS METHOD, PROGRAM, AND RECORDING MEDIUM

(71) Applicant: SEIKO EPSON CORPORATION, Tokyo (JP)

(72) Inventors: Kazuhiro Shibuya, Shiojiri (JP); Masafumi Sato, Hara-mura (JP)

(73) Assignee: SEIKO EPSON CORPORATION, Tokyo (JP)

( * ) Notice: Subject to any disclaimer, the term of this patent is extended or adjusted under 35 U.S.C. 154(b) by 43 days.

This patent is subject to a terminal disclaimer.

(21) Appl. No.: 15/973,589

(22) Filed: May 8, 2018

(65) Prior Publication Data

US 2018/0300728 A1 Oct. 18, 2018

Related U.S. Application Data

(63) Continuation of application No. 14/965,139, filed on Dec. 10, 2015, now Pat. No. 9,999,394.

(30) Foreign Application Priority Data

Dec. 22, 2014 (JP) .................... 2014-258533

(51) Int. Cl.
*A63B 69/36* (2006.01)
*G06Q 20/40* (2012.01)
(Continued)

(52) U.S. Cl.
CPC ............ *G06Q 20/4016* (2013.01); *A61B 5/11* (2013.01); *A61B 5/6895* (2013.01);
(Continued)

(58) Field of Classification Search
CPC .. G06Q 20/4016; G06Q 20/342; G06Q 20/24; G06Q 10/0639; G06K 9/00543;
(Continued)

(56) References Cited

U.S. PATENT DOCUMENTS 4,137,566 A 1/1979 Haas et al.
5,111,410 A 5/1992 Nakayama et al.
(Continued)

FOREIGN PATENT DOCUMENTS

JP 2004-135908 A 5/2004
JP 2008-073210 A 4/2008
(Continued)

OTHER PUBLICATIONS

Sep. 30, 2016 Office Action Issued in U.S. Appl. No. 14/965,139.
(Continued)

*Primary Examiner* — Nini F Legesse
(74) *Attorney, Agent, or Firm* — Oliff PLC

(57) ABSTRACT

A motion analysis device includes a first calculation unit that obtains a relation between a movement direction of a ball hitting surface of an exercise tool at a time of entering an impact and a posture of the ball hitting surface at the impact by using an output of an inertial sensor.

14 Claims, 11 Drawing Sheets

(51) Int. Cl.
  *A61B 5/11*     (2006.01)
  *G06K 9/00*     (2006.01)
  *G09B 19/00*    (2006.01)
  *G06Q 10/06*    (2012.01)
  *A61B 5/00*     (2006.01)
  *G06Q 20/24*    (2012.01)
  *G06Q 20/34*    (2012.01)
  *G06F 19/00*    (2018.01)
  *H04M 1/725*    (2006.01)
  *G16H 20/30*    (2018.01)

(52) U.S. Cl.
  CPC ..... *G06K 9/00342* (2013.01); *G06K 9/00543* (2013.01); *G06Q 10/0639* (2013.01); *G06Q 20/24* (2013.01); *G06Q 20/342* (2013.01); *G09B 19/0038* (2013.01); *A61B 2503/10* (2013.01); *G06F 19/3481* (2013.01); *G16H 20/30* (2018.01); *H04M 1/7253* (2013.01)

(58) Field of Classification Search
  CPC ........... G06K 9/00342; G09B 19/0038; G16H 20/30; H04M 1/7253; A61B 2503/10; A61B 5/6895; A61B 5/11; G06F 19/3481
  USPC ................................ 473/221–223, 226, 227
  See application file for complete search history.

(56) References Cited

U.S. PATENT DOCUMENTS

| | | | |
|---|---|---|---|
| 5,233,544 A | 8/1993 | Kobayashi | |
| 7,264,554 B2 | 9/2007 | Bentley | |
| 7,892,114 B2 | 2/2011 | Saegusa et al. | |
| 8,109,816 B1 | 2/2012 | Grober | |
| 8,565,483 B2 | 10/2013 | Nakaoka | |
| 8,672,779 B1 | 3/2014 | Sakyo et al. | |
| 8,696,482 B1 | 4/2014 | Pedenko et al. | |
| 8,876,621 B2 | 11/2014 | Shibuya | |
| 9,403,077 B2 | 8/2016 | Ota et al. | |
| 9,999,394 B2 * | 6/2018 | Shibuya | A61B 5/11 |
| 2003/0207718 A1 | 11/2003 | Perlmutter | |
| 2008/0020867 A1 | 1/2008 | Manwaring | |
| 2009/0247312 A1 | 10/2009 | Sato et al. | |
| 2011/0224012 A1 | 9/2011 | Hashimoto et al. | |
| 2012/0179418 A1 | 7/2012 | Takasugi et al. | |
| 2013/0005496 A1 | 1/2013 | Priester et al. | |
| 2014/0213382 A1 | 7/2014 | Kang et al. | |

FOREIGN PATENT DOCUMENTS

| | | |
|---|---|---|
| JP | 2010-046539 A | 3/2010 |
| JP | 2011-110164 A | 6/2011 |
| WO | 2014/092213 A1 | 6/2014 |

OTHER PUBLICATIONS

Sep. 20, 2017 Office Action Issued in U.S. Appl. No. 14/965,139.
May 11, 2017 Office Action Issued in U.S. Appl. No. 14/965,139.
Feb. 22, 2018 Notice of Allowance Issued in U.S. Appl. No. 14/965,139.
Mar. 21, 2018 Supplemental Notice of Allowance Issued in U.S. Appl. No. 14/965,139.

* cited by examiner

ANGULAR VELOCITY [dps]

TIME [ms]

COMPOSITE VALUE OF ANGULAR VELOCITY (NORMALIZED IN 0 TO 100)

TIME [ms]

DIFFERENTIAL OF COMPOSITE VALUE OF ANGULAR VELOCITY

TIME [ms]

MOTION ANALYSIS DEVICE, MOTION ANALYSIS SYSTEM, MOTION ANALYSIS METHOD, PROGRAM, AND RECORDING MEDIUM

BACKGROUND

1. Technical Field

The present invention relates to an motion analysis device, an motion analysis system, an motion analysis method, a program, and a recording medium.

2. Related Art

In a projectile line (a course of a hit ball) of a golf ball hit by a swing of a golfer, there are types of a slice, a fade, a straight, a draw, a hook, and the like. Elements for deciding the projectile line of a golf ball are an incident angle and a face angle of a club head at the time of an impact (see JP-A-2011-110164 and the like). In particular, in JP-A-2011-110164, to analyze a type of projectile line, a target line connecting the center of a golf ball and a target is specified based on a swing video photographed by a camera and an incident angle $\theta$ and a face angle $\phi$ are measured using the target line as a criterion.

In the measurement method of JP-A-2011-110164, however, since the target line is merely predicted from the video, there is a possibility of the type of projectile line not being correctly analyzed. Further, in order to improve analysis precision of the type of projectile line, it is necessary to also examine a method of calculating parameters (an incident angle $\theta$ and a face angle $\phi$) to be used for the analysis in detail.

SUMMARY

An advantage of some aspects of the invention is that it provides an motion analysis device, an motion analysis system, an motion analysis method, and a program capable of acquiring effective information for analysis or the like of a type of projectile line.

The invention can be implemented as the following forms or application example.

Application Example 1

An motion analysis device according to Application Example 1 includes a first calculation unit that obtains a relation between a movement direction of a ball hitting surface of an exercise tool at a time of entering an impact and a posture of the ball hitting surface at the time of the impact by using an output of an inertial sensor.

In the motion analysis device according to Application Example 1, it is possible to obtain effective data for the analysis of the type of projectile line.

Application Example 2

In the motion analysis device according to the application example, the first calculation unit may obtain, as the relation, an angle formed by a vector indicating the movement direction of the ball hitting surface at the time of entering the impact and a predetermined vector which lies along the ball hitting surface at the time of the impact.

Application Example 3

In the motion analysis device according to the application example, the first calculation unit may obtain, as the relation, an angle formed by the vector indicating the movement direction of the ball hitting surface at the time of entering the impact and a predetermined vector intersecting the ball hitting surface at the time of the impact.

Application Example 4

In the motion analysis device according to the application example, the first calculation unit may obtain, as the relation, an angle formed by the vector indicating the movement direction of the ball hitting surface at the time of entering the impact and the predetermined vector projected on a predetermined plane intersecting in a vertical direction.

Application Example 5

The motion analysis device according to the application example may further include a second calculation unit that obtains a relation between a posture of the ball hitting surface before exercise starts and the movement direction of the ball hitting surface at the time of entering the impact by using the output of the inertial sensor. Accordingly, the motion analysis device according to the application example can measure the posture of the ball hitting surface at the impact and the movement direction of the ball hitting surface at the time of entering the impact.

Application Example 6

The motion analysis device according to the application example may further include an output processing unit that outputs data indicating at least one of the relation obtained by the first calculation unit and the relation obtained by the second calculation unit. Accordingly, a user can confirm at least one of his or her habit related to the posture of the ball hitting surface and his or her habit related to the movement direction of the ball hitting surface as data on a graph.

Application Example 7

In the motion analysis device according to the application example, the output processing unit may display data indicating a combination of the relation obtained by the first calculation unit and the relation obtained by the second calculation unit as a two-dimensional graph. Accordingly, the user can confirm his or her type of projectile line as data on a two-dimensional graph.

Application Example 8

In the motion analysis device according to the application example, the output processing unit may display a type of projectile line predicted from the data along with the graph. Accordingly, the user can objectively recognize his or her type of projectile line.

Application Example 9

In the motion analysis device according to the application example, the output processing unit may display a map in which an area is divided in accordance with the type of projectile line along with the graph. Accordingly, the user can intuitively recognize his or her type of projectile line.

Application Example 10

In the motion analysis device according to the application example, the output processing unit may set an origin of the graph so that an area corresponding to a straight type of projectile line is located in a middle of the graph. Accordingly, for example, the user can approach his or her type of projectile line in a so-called straight manner by exercising ball hitting so that his or her data is located in the middle of the graph.

Application Example 11

In the motion analysis device according to the application example, the output processing unit may display a plurality of pieces of data regarding exercises of a plurality of times with the same graph and distinguish recent data from the other data on the graph. Accordingly, the user can compare his or her recent type of projectile line to the previous type of projectile line.

Application Example 12

An motion analysis system according to Application Example 12 includes the motion analysis device according to any one of the foregoing application examples; and the inertial sensor. Accordingly, in the motion analysis system according to Application Example 12, it is possible to obtain effective data for the analysis of the type of projectile line.

Application Example 13

An motion analysis method according to Application Example 13 includes: obtaining a relation between a movement direction of a ball hitting surface of an exercise tool at a time of entering an impact and a posture of the ball hitting surface at the time of the impact by using an output of an inertial sensor. Accordingly, in the motion analysis method according to Application Example 13, it is possible to obtain effective data for the analysis of the type of projectile line.

Application Example 14

In the motion analysis method according to the application example, in the obtaining of the relation, an angle formed by a vector indicating the movement direction of the ball hitting surface at the time of entering the impact and a predetermined vector which lies along the ball hitting surface at the time of the impact may be calculated as the relation.

Application Example 15

In the motion analysis method according to the application example, in the obtaining of the relation, an angle formed by the vector indicating the movement direction of the ball hitting surface at the time of entering the impact and a predetermined vector intersecting the ball hitting surface at the time of the impact may be calculated as the relation.

Application Example 16

In the motion analysis method according to the application example, in the obtaining of the relation, an angle formed by the vector indicating the movement direction of the ball hitting surface at the time of entering the impact and the predetermined vector projected on a predetermined plane intersecting in a vertical direction may be calculated as the relation.

Application Example 17

An motion analysis program according to Application Example 17 causes a computer to perform a posture calculation procedure of obtaining a relation between a movement direction of a ball hitting surface of an exercise tool at a time of entering an impact and a posture of the ball hitting surface at the time of the impact by using an output of an inertial sensor. Accordingly, in the motion analysis program according to Application Example 17, it is possible to obtain effective data for the analysis of the type of projectile line.

Application Example 18

A recording medium according to Application Example 18 stores an motion analysis program that causes a computer to perform a posture calculation procedure of obtaining a relation between a movement direction of a ball hitting surface of an exercise tool at a time of entering an impact and a posture of the ball hitting surface at the time of the impact by using an output of an inertial sensor.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, preferred embodiments of the invention will be described in detail with reference to the drawings. The embodiments to be described below do not inappropriately limit the content of the invention described in the appended claims. All of the constituents to be described below may not be said to be essential constituent requisites of the invention.

Hereinafter, a swing analysis system performing analysis of a golf swing will be described as an example of an motion analysis system.

1. Swing Analysis System

1-1. Overview of Swing Analysis System

Figure 1:
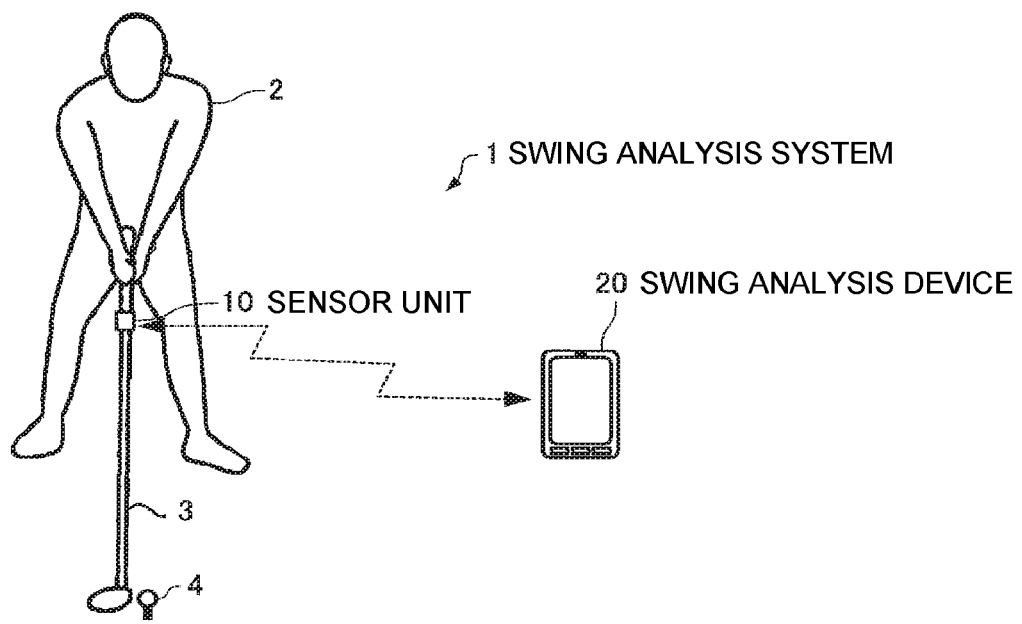
FIG. 1 is a diagram illustrating an overview of a swing analysis system which is an example of an motion analysis system according to an embodiment.

FIG. 1 is a diagram illustrating an overview of a swing analysis system according to an embodiment. A swing analysis system 1 according to the embodiment is configured to include a sensor unit 10 (which is an example of an inertial sensor) and a swing analysis device 20 (which is an example of an motion analysis device).

The sensor unit 10 can measure acceleration generated in each axis direction of three axes and an angular velocity generated in each rotation of the three axes and is mounted on a golf club 3 (which is an example of an exercise tool).

Figure 2:
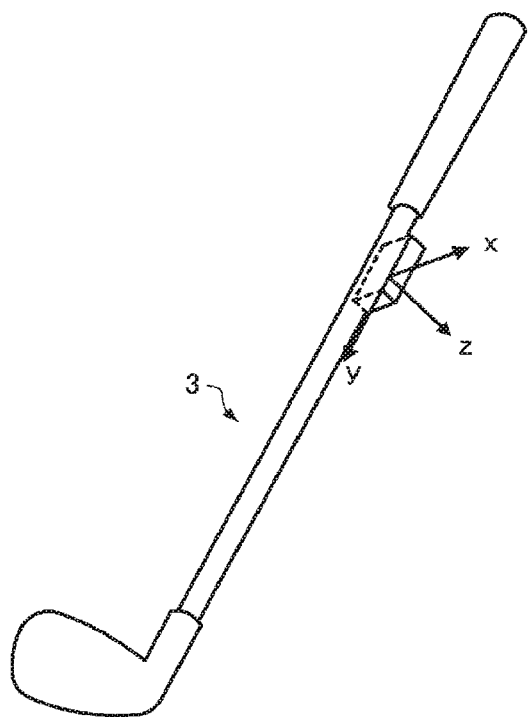
FIG. 2 is a diagram illustrating examples of a mounting position and direction of a sensor unit.

In the embodiment, as illustrated in FIG. 2, the sensor unit 10 is fitted on a part of a shaft of the golf club 3 when one axis among three detection axes (an x axis, a y axis, and a z axis), for example, the y axis, conforms to the longitudinal direction of the shaft. Preferably, the sensor unit 10 is fitted at a position close to a grip in which a shock at the time of hitting is rarely delivered and a centrifugal force is not applied at the time of swinging. The shaft is a portion of a handle excluding a head of the golf club 3 and also includes the grip.

Figure 3:
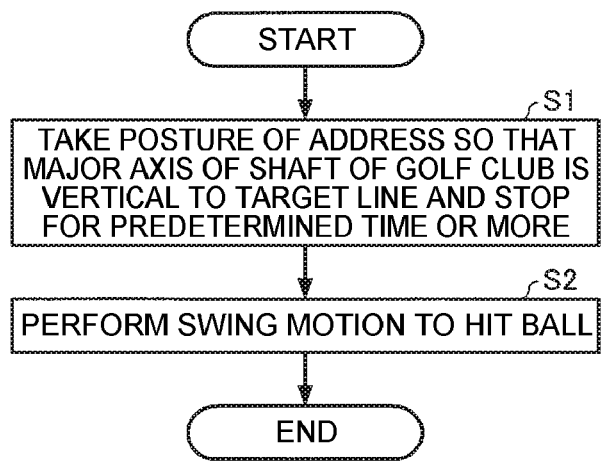
FIG. 3 is a diagram illustrating a procedure of operations performed by a user according to the embodiment.

A user 2 performs a swing motion of hitting a golf ball 4 in a pre-decided procedure. FIG. 3 is a diagram illustrating a procedure of a motion performed by the user 2. As illustrated in FIG. 3, the user 2 first holds the golf club 3, takes a posture of address so that the major axis of the shaft of the golf club 3 is vertical to a target line (target direction of hitting), and stops for a predetermined time or more (for example, 1 second or more) (S1). Next, the user 2 performs a swing motion to hit the golf ball 4 (S2).

While the user 2 performs the motion to hit the golf ball 4 in the procedure illustrated in FIG. 3, the sensor unit 10 measures triaxial acceleration and triaxial angular velocity at a predetermined period (for example, 1 ms) and sequentially transmits measurement data to the swing analysis device 20. The sensor unit 10 may immediately transmit the measurement data, or may store the measurement data in an internal memory and transmit the measurement data at a predetermined timing such as the end of a swing motion of the user 2. Communication between the sensor unit 10 and the swing analysis device 20 may be wireless communication or wired communication. Alternatively, the sensor unit 10 may store the measurement data in a recording medium such as a memory card which can be detachably mounted and the swing analysis device 20 may read the measurement data from the recording medium.

In the embodiment, the swing analysis device 20 calculates an index (which is an index of a movement direction at the time of entering an impact) θ of a movement direction of the head of the golf club 3 at an impact and an index φ' of a posture of a face surface (ball hitting surface) at the impact, using the data measured by the sensor unit 10. Then, the swing analysis device 20 displays (outputs) the indexes θ and φ' as graphs or the like to a display unit (display). The swing analysis device 20 may be, for example, a portable device such as a smartphone or a personal computer (PC).

1-2. Configuration of Swing Analysis System

Figure 4:
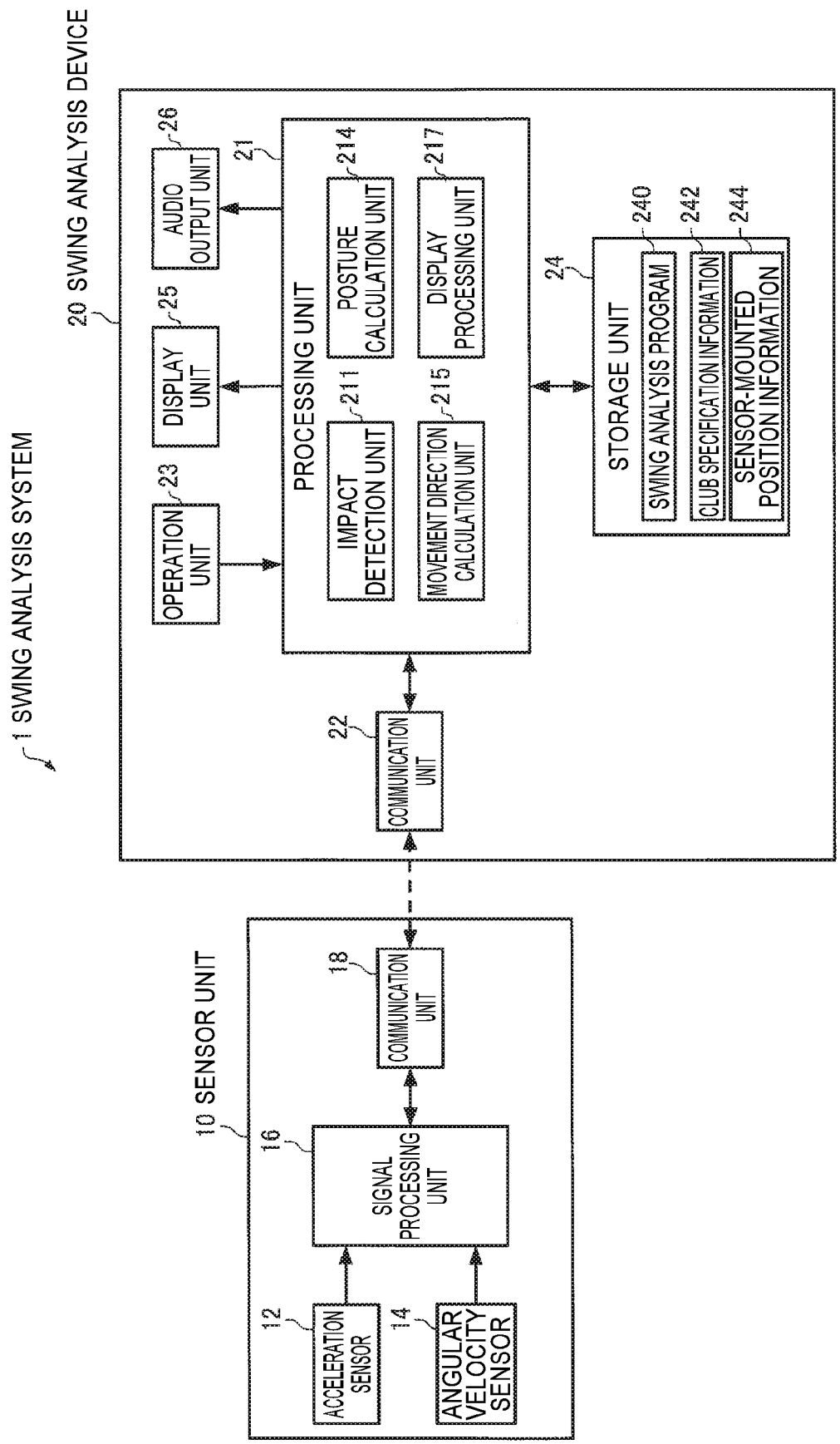
FIG. 4 is a diagram illustrating an example of the configuration of the swing analysis system according to the embodiment.

FIG. 4 is a diagram illustrating an example of the configuration of the swing analysis system 1 (examples of the configurations of the sensor unit 10 and the swing analysis device 20) according to the embodiment. As illustrated in FIG. 4, in the embodiment, the sensor unit 10 is configured to include an acceleration sensor 12, an angular velocity sensor 14, a signal processing unit 16, and a communication unit 18.

The acceleration sensor 12 measures acceleration generated in each of mutually intersecting (ideally, orthogonal) triaxial directions and outputs digital signals (acceleration data) according to the sizes and directions of the measured triaxial accelerations.

The angular velocity sensor 14 measures an angular velocity generated at axis rotation of mutually intersecting (ideally, orthogonal) triaxial directions and outputs digital signals (angular velocity data) according to the sizes and directions of the measured triaxial angular velocities.

The signal processing unit 16 receives the acceleration data and the angular velocity data from the acceleration sensor 12 and the angular velocity sensor 14, appends time information, and stores the acceleration data and the angular velocity data in a storage unit (not illustrated). The signal processing unit 16 generates packet data in conformity to a communication format by appending time information to the stored measurement data (the acceleration data and the angular velocity data) and outputs the packet data to the communication unit 18.

The acceleration sensor 12 and the angular velocity sensor 14 are ideally fitted in the sensor unit 10 so that the three axes of each sensor match the three axes (the x axis, the y axis, and the z axis) of the xyz rectangular coordinate system (sensor coordinate system $\Sigma_{xyz}$) defined for the sensor unit 10, but errors of the fitting angles actually occur. Accordingly, the signal processing unit 16 performs a process of converting the acceleration data and the angular velocity data into data of the xyz coordinate system (sensor coordinate system $\Sigma_{xyz}$) using correction parameters calculated in advance according to the errors of the fitting angles.

The signal processing unit 16 may perform a temperature correction process on the acceleration sensor 12 and the angular velocity sensor 14. Alternatively, a temperature correction function may be embedded in the acceleration sensor 12 and the angular velocity sensor 14.

The acceleration sensor 12 and the angular velocity sensor 14 may output analog signals. In this case, the signal processing unit 16 may perform A/D conversion on each of an output signal of the acceleration sensor 12 and an output signal of the angular velocity sensor 14, generate measurement data (acceleration data and angular velocity data), and generate packet data for communication using the measurement data.

The communication unit 18 performs, for example, a process of transmitting the packet data received from the signal processing unit 16 to the swing analysis device 20 or a process of receiving control commands from the swing analysis device 20 and transmitting the control commands to the signal processing unit 16. The signal processing unit 16 performs various processes according to the control commands.

The swing analysis device 20 is configured to include a processing unit 21, a communication unit 22, an operation unit 23, a storage unit 24, a display unit 25, and an audio output unit 26.

The communication unit 22 performs, for example, a process of receiving the packet data transmitted from the sensor unit 10 and transmitting the packet data to the processing unit 21 or a process of transmitting a control command from the processing unit 21 to the sensor unit 10.

The operation unit 23 performs a process of acquiring operation data from the user 2 and transmitting the operation data to the processing unit 21. The operation unit 23 may be, for example, a touch panel type display, a button, a key, or a microphone.

The storage unit 24 is configured as, for example, any of various IC memories such as a read-only memory (ROM), a flash ROM, and a random access memory (RAM) or a recording medium such as a hard disk or a memory card.

The storage unit 24 stores, for example, programs used for the processing unit 21 to perform various calculation processes or control processes, or various program or data used for the processing unit 21 to realize application functions. In particular, in the embodiment, the storage unit 24 stores a swing analysis program 240 which is read by the processing unit 21 to perform a swing analysis process. The swing analysis program 240 may be stored in advance in a non-volatile recording medium. Alternatively, the swing analysis program 240 may be received from a server via a network by the processing unit 21 and may be stored in the storage unit 24.

In the embodiment, the storage unit 24 stores club specification information 242 indicating the specification of the golf club 3 and sensor-mounted position information 244. For example, the user 2 operates the operation unit 23 to input a model number of the golf club 3 (or selects the model number from a model number list) to be used and sets specification information regarding the input model number as the club specification information 242 among pieces of specification information for each model number (for example, information regarding the length of a shaft, the position of the center of gravity, a lie angle, a face angle, a loft angle, and the like) stored in advance in the storage unit 24. Alternatively, by mounting the sensor unit 10 at a decided predetermined position (for example, a distance of 20 cm from the grip), information regarding the predetermined position may be stored in advance as the sensor-mounted position information 244.

The storage unit 24 is used as a work area of the processing unit 21 and temporarily stores, for example, data input from the operation unit 23 and calculation results performed according to various programs by the processing unit 21. The storage unit 24 may store data necessarily stored for a long time among the data generated through the processes of the processing unit 21.

The display unit 25 displays a processing result of the processing unit 21 as text, a graph, a table, animations, or another image. The display unit 25 may be, for example, a CRT, an LCD, a touch panel type display, or a head-mounted display (HMD). The functions of the operation unit 23 and the display unit 25 may be realized by one touch panel type display.

The audio output unit 26 outputs a processing result of the processing unit 21 as audio such as a voice or a buzzer sound. The audio output unit 26 may be, for example, a speaker or a buzzer.

The processing unit 21 performs a process of transmitting a control command to the sensor unit 10, various calculation processes on data received from the sensor unit 10 via the communication unit 22, and other various control processes according to various programs. In particular, in the embodiment, the processing unit 21 performs the swing analysis program 240 to function as an impact detection unit 211, a posture calculation unit (which is an example of a first calculation unit) 214, a movement direction calculation unit (which is an example of a second calculation unit) 215, and a display processing unit (which is an example of an output processing unit) 217.

For example, the processing unit 21 performs processes of receiving the packet data received by the communication unit 22 from the sensor unit 10, acquiring time information and measurement data from the received packet data, and storing the time information and the measurement data in the storage unit 24 in association therewith.

The processing unit 21 performs, for example, a process of detecting a timing (measurement time of measurement data) of an impact in a swing of the user 2, using the measurement data.

The processing unit 21 performs a process of generating time-series data indicating a change in the posture of the sensor unit 10 by applying the angular velocity data included in the measurement data to, for example, a predetermined calculation formula (the change in the posture can also be expressed by, for example, rotation angles (a roll angle, a pitch angle, and a yaw angle) of axial directions, quaternions, or a rotation matrix).

The processing unit 21 performs a process of generating time-series data indicating a change in the position of the sensor unit 10 by performing, for example, time integration on the acceleration data included in the measurement data (the change in the position can also be expressed by, for example, a velocity in each axial direction (velocity vector)).

The processing unit 21 performs, for example, a process of generating time-series data indicating a change in the posture of the face surface of the golf club 3 based on the time-series data indicating the change in the posture of the sensor unit 10, the club specification information 242, and the sensor-mounted position information 244.

The processing unit 21 performs, for example, a process of generating time-series data indicating a change in the position of the face surface of the golf club 3 based on the time-series data indicating the change in the position of the sensor unit 10, the time-series data indicating the change in the posture of the sensor unit 10, the club specification information 242, and the sensor-mounted position information 244.

Here, the processing unit 21 according to the embodiment performs, for example, the following processes (1) to (6) to measure the posture and the position of the face surface at each time point using the time of stopping of the user 2 (address measurement time $t_0$) as a criterion.

(1) The processing unit 21 corrects a bias by calculating an offset amount included in the measurement data using measurement data (acceleration data and angular velocity data) at time $t_0$ and subtracting the offset amount from measurement data (acceleration data and angular velocity data) at a swing.

Figure 5:
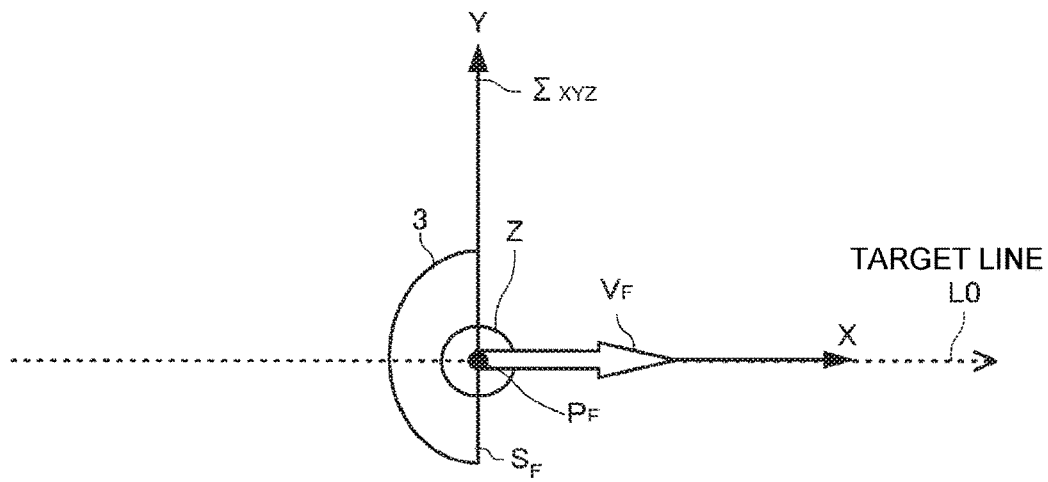
FIG. 5 is a diagram illustrating a relation between a global coordinate system $\Sigma_{XYZ}$ and a head in an address.

(2) The processing unit 21 decides an XYZ orthogonal coordinate system (global coordinate system $\Sigma_{XYZ}$) to be fixed to the ground based on the acceleration data (that is, data indicating the direction of gravity acceleration) at time $t_0$, the club specification information 242, and the sensor-mounted position information 244. For example, as illustrated in FIG. 5, the origin of the global coordinate system $\Sigma_{XYZ}$ is set at the position of the head at time $t_0$, the Z axis of the global coordinate system $\Sigma_{XYZ}$ is set in the upward vertical direction (that is, an opposite direction to the direction of the gravity acceleration), and the X axis of the global coordinate system $\Sigma_{XYZ}$ is set in the same direction as the x axis of the sensor coordinate system $\Sigma_{xyz}$ at time $t_0$. Accordingly, in this case, the X axis of the global coordinate system $\Sigma_{XYZ}$ can be considered to be a target line L0.

(3) The processing unit 21 decides a face vector $V_F$ indicating the posture of a face surface $S_F$. A method of adopting the face vector $V_F$ is arbitrary. In the embodiment, however, as illustrated in FIG. 5, a unit vector (which is an example of a predetermined vector intersecting the face surface (ball hitting surface)) oriented in the +X axis direction at time $t_0$ is used as the face vector $V_F$. In this case, at time $t_0$, a Y axis component and a Z axis component of the face vector $V_F$ are zero.

(4) The processing unit 21 sets the face vector $V_F$ at time $t_0$ in the global coordinate system $\Sigma_{XYZ}$ as an initial face vector $V_F(t_0)$ and calculates a face vector $V_F(t)$ at each time in the global coordinate system $\Sigma_{XYZ}$ based on the initial face vector $V_F(t_0)$ and the time-series data (after the correction of the bias) indicating a change in the posture of the face surface $S_F$.

(5) The processing unit 21 decides face coordinates $P_F$ indicating the position of the face surface $S_F$. A method of adopting the face coordinates $P_F$ is arbitrary. In the embodiment, a point located at the origin of the global coordinate system $\Sigma_{XYZ}$ at time $t_0$ is assumed to be the face coordinates $P_F$. In this case, as illustrated in FIG. 5, the X axis component, the Y axis component, and the Z axis component of the face coordinates $P_F$ at time $t_0$ are zero.

(6) The processing unit 21 sets the face coordinates $P_F$ at time $t_0$ in the global coordinate system $\Sigma_{XYZ}$ as initial face coordinates $P_F(t_0)$ and calculates face coordinates $P_F(t)$ at each time in the global coordinate system $\Sigma_{XYZ}$ based on the initial face coordinates $P_F(t_0)$ and time-series data (after correction of the bias) indicating a change in the position of the face surface $S_F$.

Here, the correction of the bias of the measurement data is performed by the processing unit 21, but may be performed by the signal processing unit 16 of the sensor unit 10. A function of correcting the bias may be embedded in the acceleration sensor 12 and the angular velocity sensor 14.

The processing unit 21 performs a process of reading/writing various programs or various kinds of data from/on the storage unit 24. The processing unit 21 also performs not only a process of storing the time information and the measurement data received from the communication unit 22 in the storage unit 24 in association therewith but also a process of storing various kinds of calculated information or the like in the storage unit 24.

The processing unit 21 performs a process of causing the display unit 25 to display various images (images, text, signs, or the like corresponding to motion analysis information (information such as the incident angle θ and the relative face angle φ' (which are examples of relations between a posture and a movement direction of a face plane)) generated by the processing unit 21). For example, the display processing unit 217 causes the display unit 25 to display the images, texts, or the like corresponding to the motion analysis information (information such as the incident angle θ and the relative face angle φ') generated by the processing unit 21 after end of the swing exercise of the user 2, automatically, or according to an input operation of the user 2. Alternatively, a display unit may be provided in the sensor unit 10, and the display processing unit 217 may transmit image data to the sensor unit 10 via the communication unit 22 and cause the display unit of the sensor unit 10 to display various images, text, or the like.

The processing unit 21 performs a process of causing the audio output unit 26 to output various kinds of audio (including a voice and a buzzer sound). For example, the processing unit 21 may read various kinds of information stored in the storage unit 24 and output audio or a voice for swing analysis to the audio output unit 26 after the end of the swing exercise of the user 2, automatically, or at the time of performing a predetermined input operation. Alternatively, an audio output unit may be provided in the sensor unit 10, and the processing unit 21 may transmit various kinds of audio data or voice data to the sensor unit 10 via the communication unit 22 and cause the audio output unit of the sensor unit 10 to output various kinds of audio or voices.

A vibration mechanism may be provided in the swing analysis device 20 or the sensor unit 10 and the vibration mechanism may also convert various kinds of analysis information into vibration information and suggest the vibration information to the user 2.

1-3. Process of Swing Analysis Device

Swing Analysis Process

Figure 6:
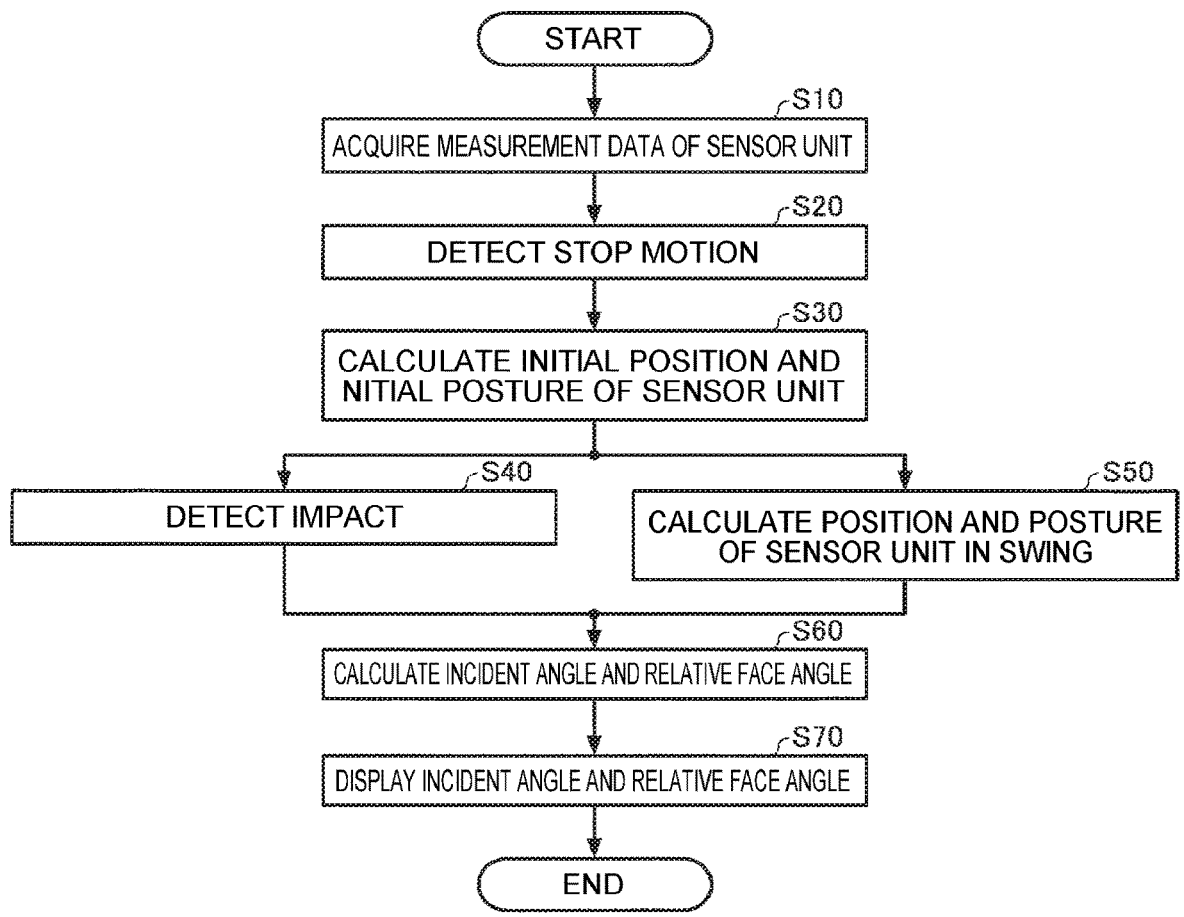
FIG. 6 is a flowchart illustrating an example of a procedure of a swing analysis process according to the embodiment.

FIG. 6 is a flowchart illustrating an example of a procedure of the swing analysis process performed by the processing unit 21 of the swing analysis device 20 according to the embodiment. The processing unit 21 of the swing analysis device 20 (which is an example of a computer) executes the swing analysis program 240 stored in the storage unit 24 to perform the swing analysis process in the procedure of the flowchart of FIG. 6. Hereinafter, the flowchart of FIG. 6 will be described.

First, the processing unit 21 acquires the measurement data of the sensor unit 10 (S10). In step S10, the processing unit 21 may perform processes subsequent to step S20 in real time when the processing unit 21 acquires the first measurement data in a swing (also including a stopping motion) of the user 2 or may perform the processes subsequent to step S20 after the processing unit 21 acquires some or all of a series of measurement data in the swing exercise of the user 2 from the sensor unit 10.

Next, the processing unit 21 detects a stopping motion (address motion) (the motion of step S1 of FIG. 3) of the user 2 using the measurement data acquired from the sensor unit 10 (S20). When the processing unit 21 performs the process in real time and detects the stopping motion (address motion), for example, the processing unit 21 may output a predetermined image or audio, or an LED may be provided in the sensor unit 10 and the LED may be turned on. Then, the user 2 is notified of detection of a stopped state, and then the user 2 may start a swing after the user 2 confirms the notification.

Next, the processing unit 21 calculates the initial position and the initial posture of the sensor unit 10 using the measurement data (the measurement data in the stopping motion (address motion) of the user 2) acquired from the sensor unit 10, the club specification information 242, the sensor-mounted position information 244, and the like (S30).

Next, the processing unit 21 detects each impact of the swing using the measurement data acquired from the sensor unit 10 (S40). An example of the procedure of the impact detection process will be described below.

The processing unit 21 calculates the position and the posture of the sensor unit 10 in the swing in parallel to, before, or after the process of step S40 using the measurement data acquired from the sensor unit 10 (S50).

Next, the processing unit 21 calculates the incident angle θ and the relative face angle φ' of the face surface $S_F$ at the time of an impact using the position and the posture of the sensor unit 10 at the time of the impact, the position of the sensor unit 10 immediately before or immediately after the impact, the club specification information 242, the sensor-mounted position information 244, and the like (S60). An example of a calculation procedure of the incident angle θ and the relative face angle φ' will be described below.

Next, the processing unit 21 generates image data indicating the incident angle θ and the relative face angle φ' calculated in step S60 and causes the display unit 25 to display the image data (S70), and then the process ends. An example of the procedure of the display process will be described below.

In the flowchart of FIG. 6, the sequence of the steps may be appropriately changed within a possible range.

Impact Detection Process

Figure 7:
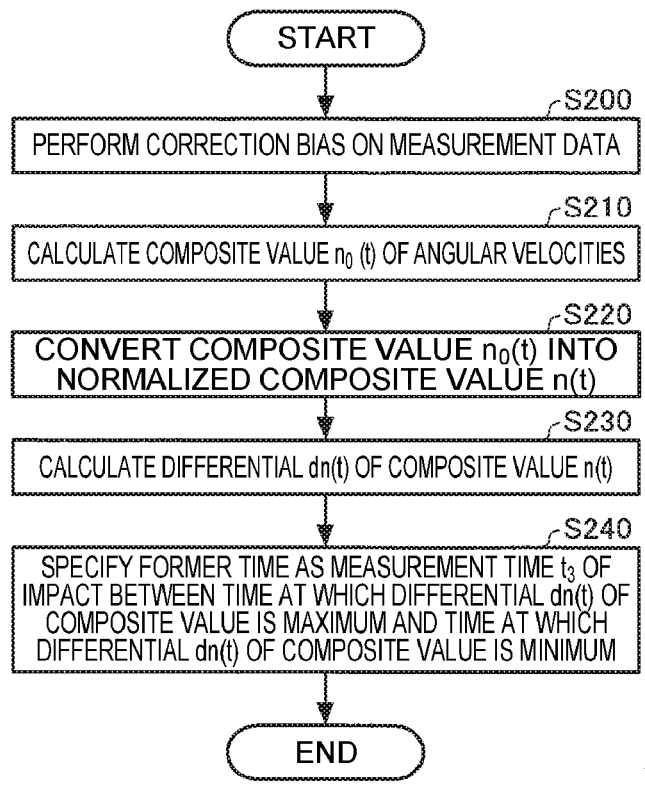
FIG. 7 is a flowchart illustrating an example of a procedure of a process of detecting an impact.

FIG. 7 is a flowchart illustrating an example of a procedure of the impact detection process (the process of step S40 of FIG. 6) in a swing of the user 2. The impact detection process corresponds to an operation of the processing unit 21 serving as the impact detection unit 211. Hereinafter, the flowchart of FIG. 7 will be described.

First, the processing unit 21 performs bias correction on the measurement data (acceleration data and angular velocity data) stored in the storage unit 24 (S200).

Next, the processing unit 21 calculates a composite value $n_0(t)$ of the angular velocities at each time t using the angular velocity data (angular velocity data at each time t) subjected to the bias correction in step S200 (S210). For example, when the angular velocity data at time t is assumed to be $x(t)$, $y(t)$, and $z(t)$, the composite value $n_0(t)$ of the angular velocities is calculated in the following formula (1).

$$n_0(t) = \sqrt{x(t)^2 + y(t)^2 + z(t)^2} \quad (1)$$

Figure 8A:
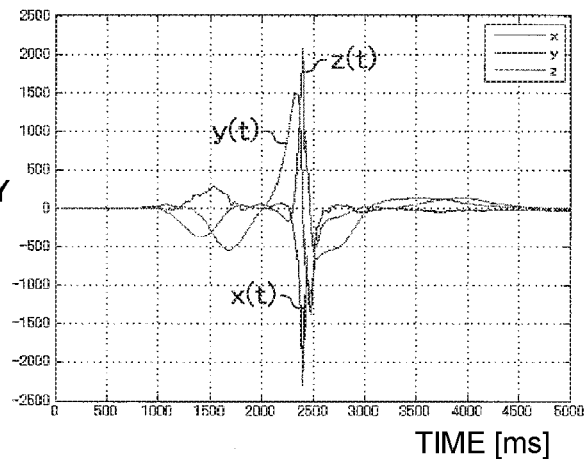
FIG. 8A is a diagram illustrating a graph of triaxial angular velocities at the time of a swing.

Examples of triaxial angular velocity data $x(t)$, $y(t)$, and $z(t)$ when the user 2 performs a swing to hit the golf ball 4 are illustrated in FIG. 8A. In FIG. 8A, the horizontal axis represents a time (msec) and the vertical axis represents the angular velocity (dps).

Next, the processing unit 21 converts the composite value $n_0(t)$ of the angular velocities at each time t into a composite value $n(t)$ subjected to normalization (scale conversion) within a predetermined range (S220). For example, when $\max(n_0)$ is the maximum value of the composite value of the angular velocities during an acquisition period of the measurement data, the composite value $n_0(t)$ of the angular velocities is converted into the composite value $n(t)$ normalized within a range of 0 to 100 by the following formula (2).

$$n(t) = \frac{100 \times n_0(t)}{\max(n_0)} \quad (2)$$

Figure 8B:
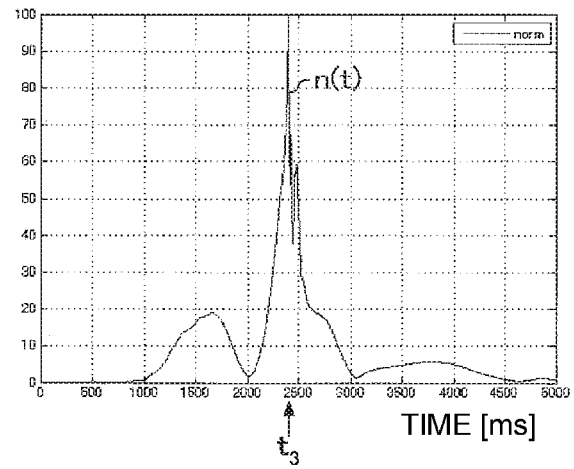
FIG. 8B is a diagram illustrating a graph of composite values of the triaxial angular velocities.

FIG. 8B is a diagram illustrating a graph of the composite value $n(t)$ normalized from 0 to 100 according to formula (2) after the composite value $n_0(t)$ of the triaxial angular velocities is calculated from the triaxial angular velocity data $x(t)$, $y(t)$, and $z(t)$ of FIG. 8A according to formula (1). In FIG. 8B, the horizontal axis represents a time (msec) and the vertical axis represents a composite value of angular velocities.

Next, the processing unit 21 calculates a differential $dn(t)$ of the composite value $n(t)$ after the normalization at each time t (S230). For example, when $\Delta t$ is a measurement period of the triaxial angular velocity data, the differential (difference) $dn(t)$ of the composite value of the angular velocity at time t is calculated in the following formula (3).

$$dn(t) = n(t) - n(t - \Delta t) \quad (3)$$

Figure 8C:
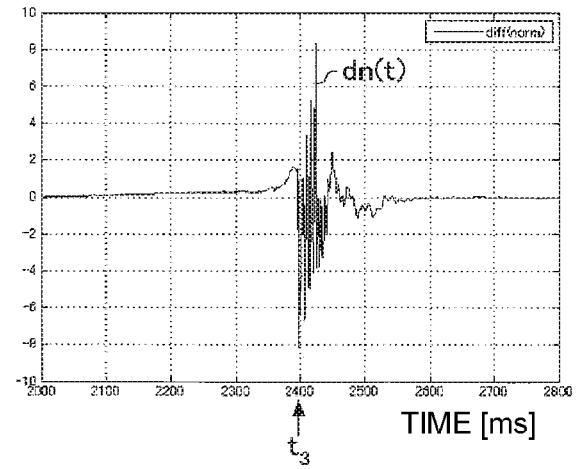
FIG. 8C is a diagram illustrating a graph of differential values of composite values of the triaxial angular velocities.

FIG. 8C is a diagram illustrating a graph obtained by calculating the differential $dn(t)$ from the composite value $n(t)$ of the triaxial angular velocities in FIG. 8B according to formula (3). In FIG. 8C, the horizontal axis represents a time (msec) and the vertical axis represents a differential value of the composite value of the triaxial angular velocities. In FIGS. 8A and 8B, the horizontal axis is shown from 0 seconds to 5 seconds. In FIG. 8C, the horizontal axis is shown from 2 seconds to 2.8 seconds so that a change in the differential value before and after the impact can be known.

Next, the processing unit 21 specifies the former time as measurement time $t_3$ of the impact between a time at which the value of the differential $dn(t)$ of the composite value is the maximum and a time at which the value of the differential $dn(t)$ of the composite value is the minimum (S240) (see FIG. 8C). In a normal golf swing, a swing velocity is considered to be the maximum at a moment of an impact. Then, since the composite value of the angular velocity is considered to be changed according to the swing velocity, a timing at which the differential value of the composite value of the angular velocity in a series of swing motions is the maximum or the minimum (that is, a timing at which the differential value of the composite value of the angular velocities is the positive maximum value or the negative minimum value) can be captured as the timing of the impact. Since the golf club 3 is vibrated due to the impact, the timing at which the differential value of the composite value of the angular velocities is the maximum is considered to be paired with the timing at which the differential value of the composite value of the angular velocities is the minimum. The former timing between the timings is considered to be the moment of the impact.

In the flowchart of FIG. 7, the sequence of the steps can be appropriately changed within a possible range. In the flowchart of FIG. 7, the processing unit 21 specifies the impact and the like using the triaxial angular velocity data, but can also specify the impact and the like similarly using triaxial acceleration data.

Process of Calculating θ and φ'

Figure 9:
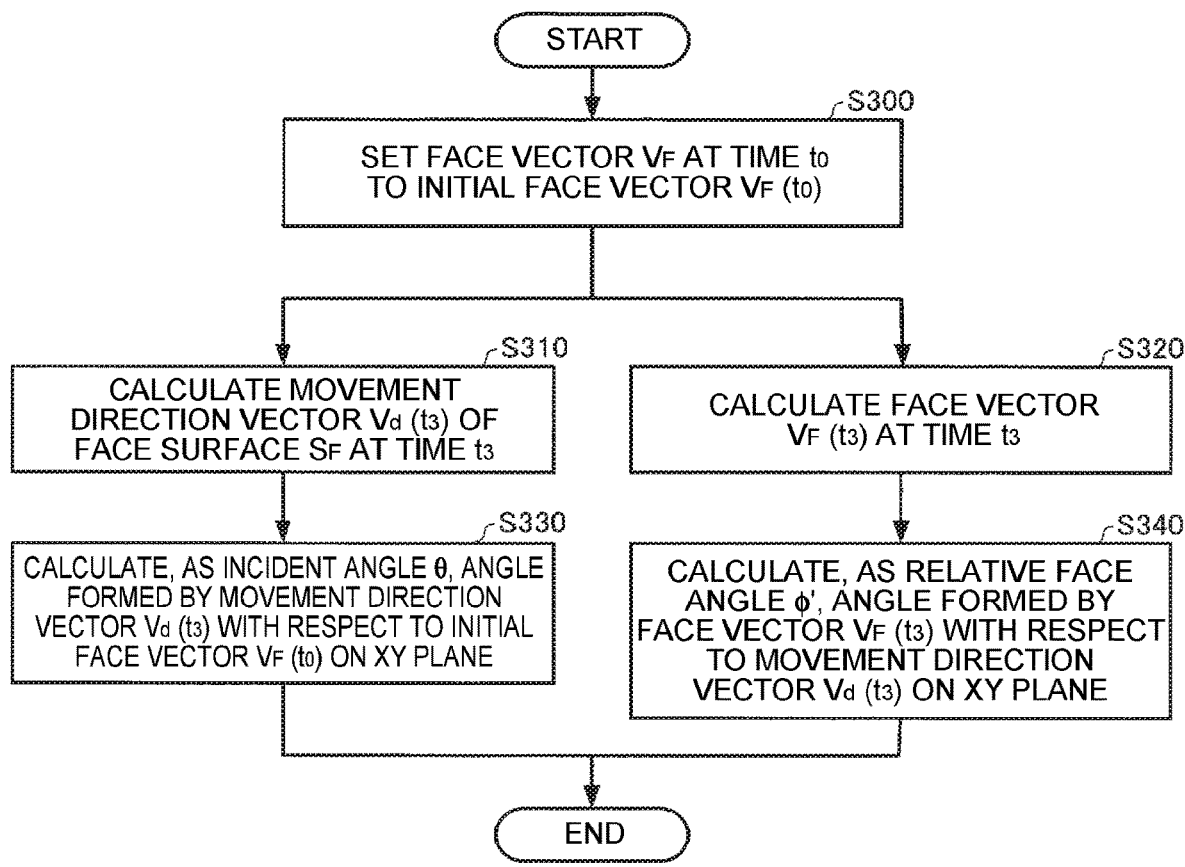
FIG. 9 is a flowchart illustrating an example of a procedure of a process (step S60 of FIG. 6) of calculating an incident angle $\theta$ and a relative face angle $\phi'$.

FIG. 9 is a flowchart illustrating an example of a procedure of a process (step S60 of FIG. 6) of calculating the incident angle θ and the relative face angle φ'. An operation of the processing unit 21 serving as the posture calculation unit 214 mainly corresponds to steps S320 and S340. A process of the processing unit 21 serving as the movement direction calculation unit 215 mainly corresponds to steps S310 and S330. Hereinafter, the flowchart of FIG. 9 will be described.

Figure 10:
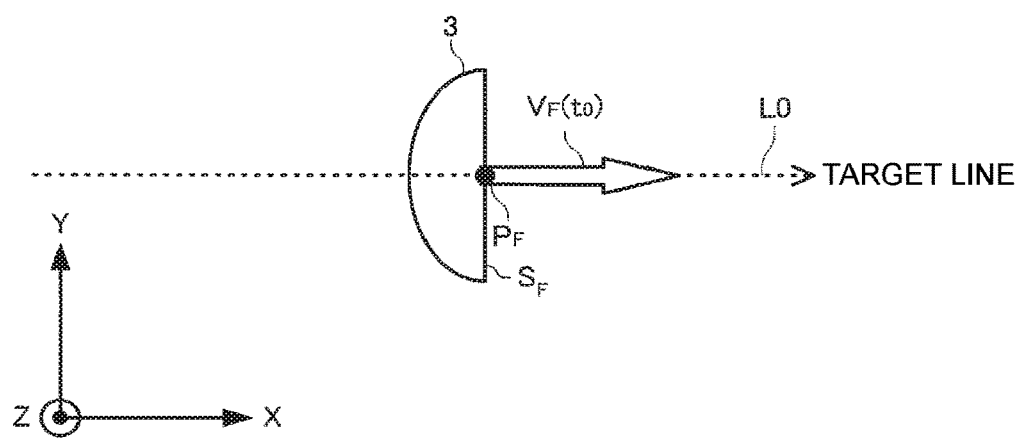
FIG. 10 is a diagram illustrating a face vector in an address.

As illustrated in FIG. 10, the processing unit 21 first sets the face vector $V_F$ at measurement time $t_0$ of the address to the initial face vector $V_F(t_0)$ (S300). As described above, the Y axis component of the initial face vector $V_F(t_0)$ is zero.

Figure 11:
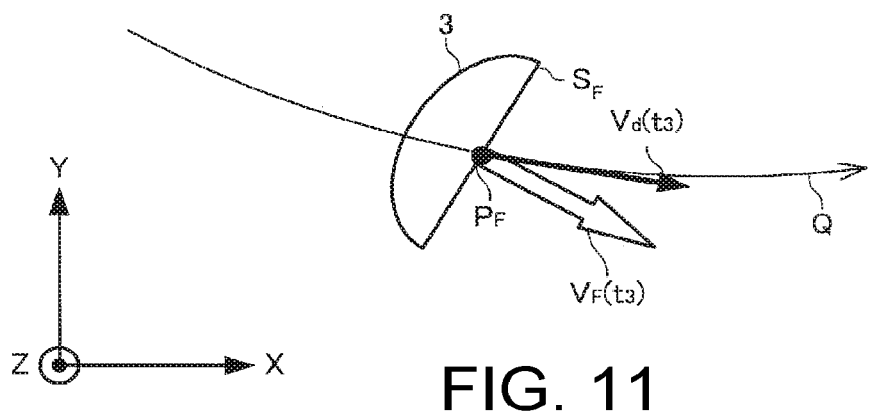
FIG. 11 is a diagram illustrating a movement direction vector and a face vector at the time of entering an impact.

Next, as illustrated in FIG. 11, the processing unit 21 calculates a movement direction vector $V_d(t_3)$ of the face surface $S_F$ at measurement time $t_3$ of an impact (S310). The movement direction vector $V_d(t_3)$ is, for example, a unit vector oriented in the same direction as a vector in which face coordinates $P_F(t_3)$ at time $t_3$ are a starting point and face coordinates $P_F(t_3 + \Delta t)$ at time $(t_3 + \Delta t)$ are an ending point. The direction of the movement direction vector $V_d(t_3)$ indicates an approximate tangential direction of a trajectory Q of the face coordinates $P_F$ projected to the XY plane at time $t_3$.

As illustrated in FIG. 11, the processing unit 21 calculates the face vector $V_F(t_3)$ of the face surface $S_F$ at time $t_3$ (S320). For example, the face vector $V_F(t_3)$ can be obtained from the initial face vector $V_F(t_0)$ and posture change data of the face surface during a period from time $(t_0 + \Delta t)$ to time $t_3$.

Figure 12:
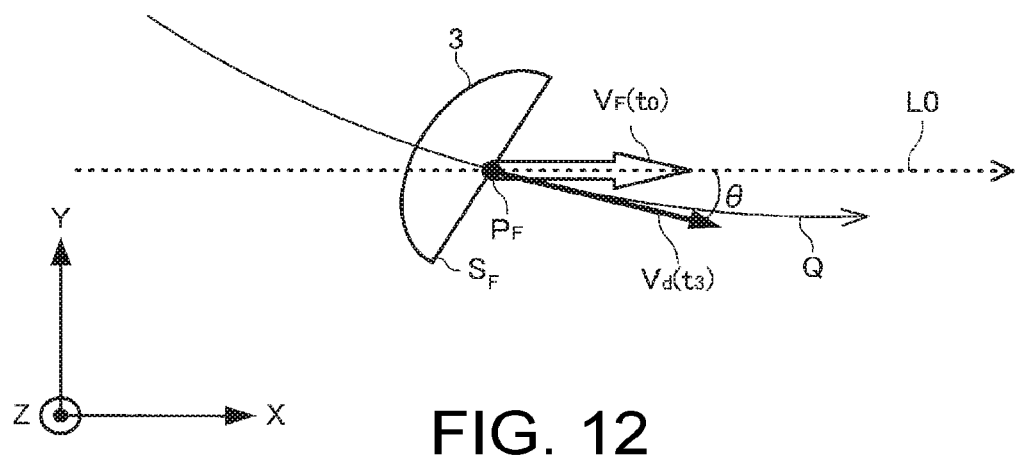
FIG. 12 is a diagram illustrating the incident angle $\theta$.

As illustrated in FIG. 12, the processing unit 21 calculates, as the incident angle θ of the face surface $S_F$, an angle formed by the initial face vector $V_F(t_0)$ projected to the XY plane (which is an example of a predetermined plane) with respect to the movement direction vector $V_d(t_3)$ projected to the XY plane (which is an example of the predetermined plane). That is, the processing unit 21 calculates, as the incident angle θ of the face surface $S_F$, an angle formed by the initial face vector $V_F(t_0)$ and the movement direction vector $V_d(t_3)$ on the XY plane (which is an example of the predetermined plane) (S330). The incident angle θ is an angle of the tangential line of the trajectory Q at time $t_3$ with respect to the target line L0 on the XY plane.

Here, as illustrated in FIG. 12, when a relation of the trajectory Q with respect to the target line L0 is so-called "inside out", the incident angle θ is positive. When the relation is so-called "inside in", the incident angle θ is zero. When the relation is so-called "outside in", the incident angle θ is negative. In this way, the direction of θ is assumed to be decided. The trajectory Q illustrated in FIG. 12 is a trajectory of the right-handed golf club 3 and the state of the trajectory Q is shown when the relation of the trajectory Q with respect to the target line L0 is so-called "inside out" (when θ is positive).

Figure 13:
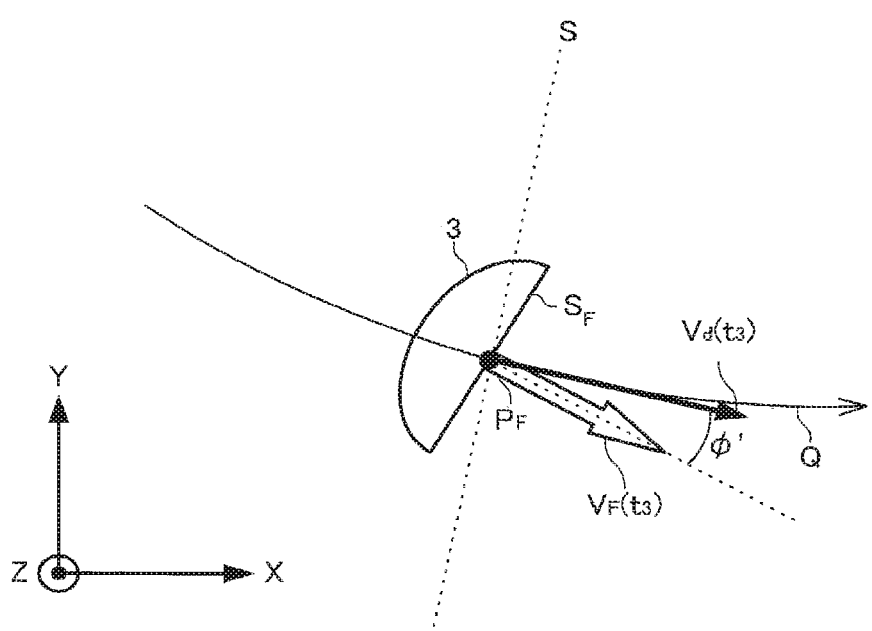
FIG. 13 is a diagram illustrating the relative face angle $\phi'$.

As illustrated in FIG. 13, the processing unit 21 calculates, as the relative face angle φ' of the face surface $S_F$, an angle formed by a face vector $V_F(t_3)$ projected to the XY plane (which is an example of the predetermined plane) with respect to the movement direction vector $V_d(t_3)$ projected to the XY plane (which is an example of the predetermined plane). That is, the processing unit 21 calculates, as the relative face angle φ' of the face surface $S_F$, an angle formed by the movement direction vector $V_d(t_3)$ and the face vector $V_F(t_3)$ on the XY plane (which is an example of the predetermined plane) (S340). Then, the processing unit 21 ends the process. The relative face angle φ' indicates a posture relation between the vertical surface (square surface S) of the trajectory Q and the face surface $S_F$ at time $t_3$.

Here, when the posture of the face surface $S_p$ with respect to the square surface S is so-called "open", the relative face angle φ' is positive. When the posture is so-called "square", the relative face angle φ' is zero. When the posture is so-called "closed", the relative face angle φ' is negative. In this way, a method of adopting φ' is assumed to be decided. The trajectory Q illustrated in FIG. 13 is a trajectory formed by the right-handed golf club 3 and the state of the trajectory Q is shown when the posture of the face surface SF is so-called "open" (when φ' is positive).

In the flowchart of FIG. 9, a sequence of the processes can be appropriately changed within a possible range.

Process of Displaying θ and φ'

Figure 14:
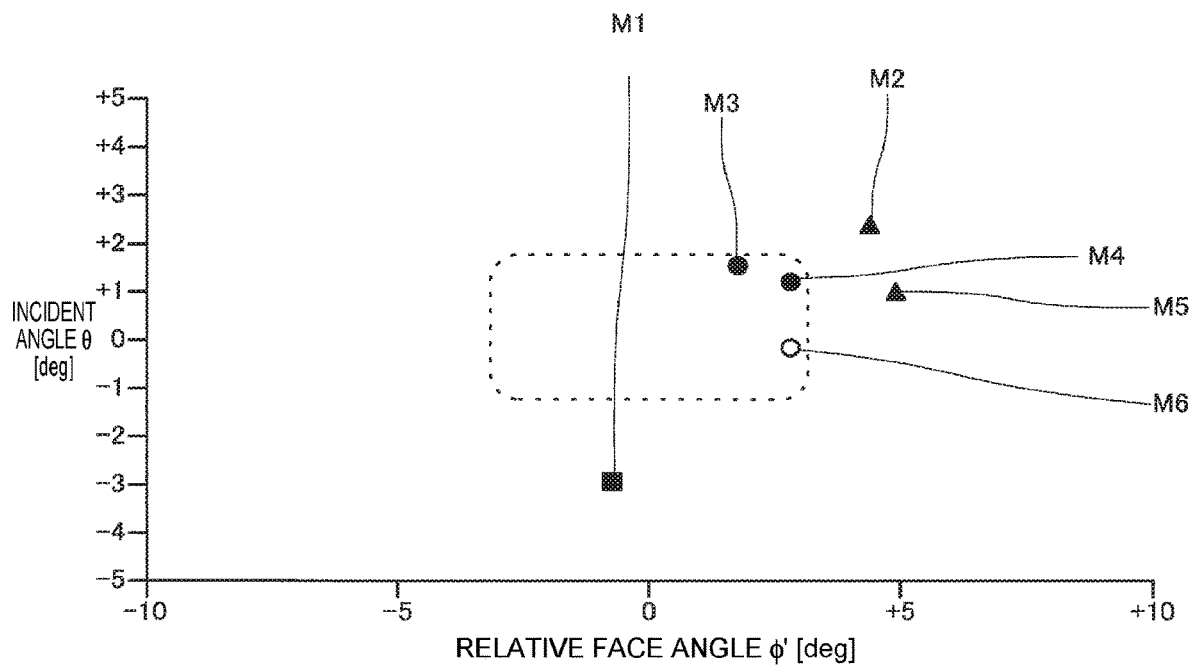
FIG. 14 is a diagram illustrating an example of a process of displaying $\theta$ and $\phi'$.

FIG. 14 is a diagram illustrating an example of a process of displaying the incident angle θ and the relative face angle φ'. An example of the display process described here corresponds to an operation of the processing unit 21 serving as the display processing unit 217.

The processing unit 21 displays data indicating combinations of θ and φ' on the display unit 25, for example, by plotting the data on a two-dimensional graph having θ and φ' axes, as illustrated in FIG. 14. In FIG. 14, plot destinations of marks M indicate the combination of θ and φ'.

In the example of FIG. 14, marks Mi (where i= 1, 2, . . . ) regarding a plurality of swings performed by the same user are plotted on the same graph and the shape of the individual mark Mi indicates a type of projectile line of the swing corresponding to the mark Mi. In FIG. 14, for example, marks M2 and M5 corresponding to a so-called push, slice, or fade-based type of projectile line are expressed with a triangular mark, a mark M1 corresponding to a so-called pull, hook, or draw-based type of projectile line is expressed with a rectangular mark, and marks M3, M4, and M6 corresponding to a so-called straight-based type of projectile line are expressed with a circular mark.

Accordingly, the user 2 can confirm the type of projectile line of an i-th swing in accordance with the plot destination of the mark Mi and the shape of the mark Mi.

In the example of FIG. 14, the recent mark M6 is displayed so that the mark M6 is distinguished by a different form (for example, inverse display, blinking display, or different color display) from the other marks M1 to M5.

Accordingly, the user 2 can distinguish his or her recent type of projectile line from the previous types of projectile lines.

Hereinafter, an example of a method in which the processing unit 21 predicts the type of projectile line from the plot destination (the combination of θ and φ') of the mark Mi will be described.

First, when the plot destination (the combination of θ and φ') of the mark Mi enters within a predetermined area (dotted line range) located near the origin, the processing unit 21 predicts that the i-th type of projectile line is a so-called straight-based type of projectile line.

When the plot destination (the combination of θ and φ') of the mark Mi is deviated from the +θ side or the +φ' side of the predetermined area (the dotted line range), the processing unit 21 predicts that the i-th type of projectile line is a so-called push, slice, or fade-based type of projectile line.

When the plot destination of the mark Mi is deviated from the −θ side or the −φ' side of the predetermined area (the dotted line range), the processing unit 21 predicts that the i-th type of projectile line is a so-called pull, hook, or draw-based type of projectile line.

In FIG. 14, the contour line of the predetermined area is drawn with a dotted line. However, the contour line of the predetermined area may not be displayed on an actual graph. In addition, when the contour line is displayed on the graph, the contour line can be used as a target of the user targeting a so-called straight-based swing.

In FIG. 14, the type of projectile line is indicated with the shape of the mark Mi, but may be indicated with a color of the mark Mi or may be indicated by a combination of the color and shape of the mark Mi. As the shapes of the marks, various shapes such as a cross and an X form can be used in addition to the rectangular shape, the triangular shape, and the circular shape.

Figure 15:
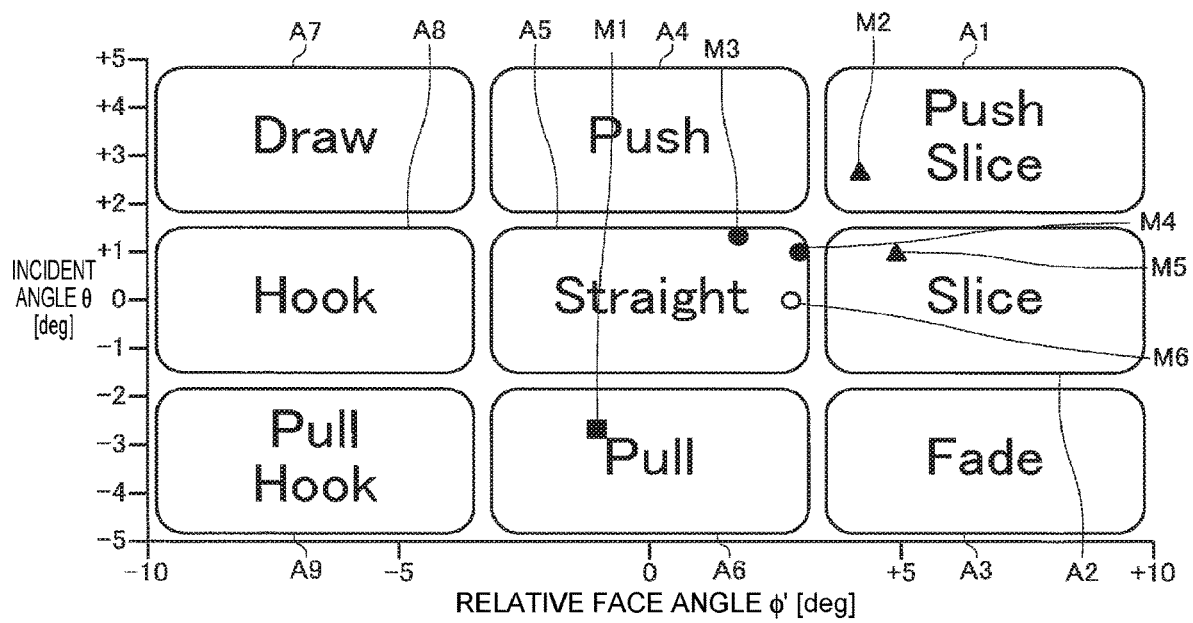
FIG. 15 is a diagram illustrating a display example of a projectile line prediction map in a background of a graph.

The processing unit 21 may display, for example, a projectile line prediction map illustrated in FIG. 15 as the background of the above-described two-dimensional graph. The projectile line prediction map is divided into areas, and text images or the like of the names of the types of projectile lines corresponding to the areas are assigned in the areas.

For example, as illustrated in FIG. 15, the projectile line prediction map is divided into 9 areas A1 to A9 arrayed in a matrix form of 3 rows and 3 columns.

In the projectile line prediction map, a text image "Straight" of the type of projectile line "straight" corresponding to the area A5 is assigned to the area A5 located in the middle near the origin.

In the projectile line prediction map, a text image "Push" of the type of projectile line "push" corresponding to the area A4 is assigned to the area A4 located on the +θ side of the area A5.

In the projectile line prediction map, a text image "Pull" of the type of projectile line "pull" corresponding to the area A6 is assigned to the area A6 located on the −θ side of the area A5.

Further, a text image "Push Slice" of the type of projectile line "push slice" corresponding to the area A1 is assigned to the area A1 located on the +ϕ' side of the area A4 of the projectile line prediction map.

Further, a text image "Slice" of the type of projectile line "slice" corresponding to the area A2 is assigned to the area A2 located on the +ϕ' side of the area A5 of the projectile line prediction map.

Further, a text image "Fade" of the type of projectile line "fade" corresponding to the area A3 is assigned to the area A3 located on the +ϕ' side of the area A6 of the projectile line prediction map.

Further, a text image "Draw" of the type of projectile line "draw" corresponding to the area A7 is assigned to the area A7 located on the −ϕ' side of the area A4 of the projectile line prediction map.

Further, a text image "Hook" of the type of projectile line "hook" corresponding to the area A8 is assigned to the area A8 located on the −ϕ' side of the area A5 of the projectile line prediction map.

Further, a text image "Pull Hook" of the type of projectile line "pull hook" corresponding to the area A9 is assigned to the area A9 located on the −ϕ' side of the area A6 of the projectile line prediction map.

Figure 16:
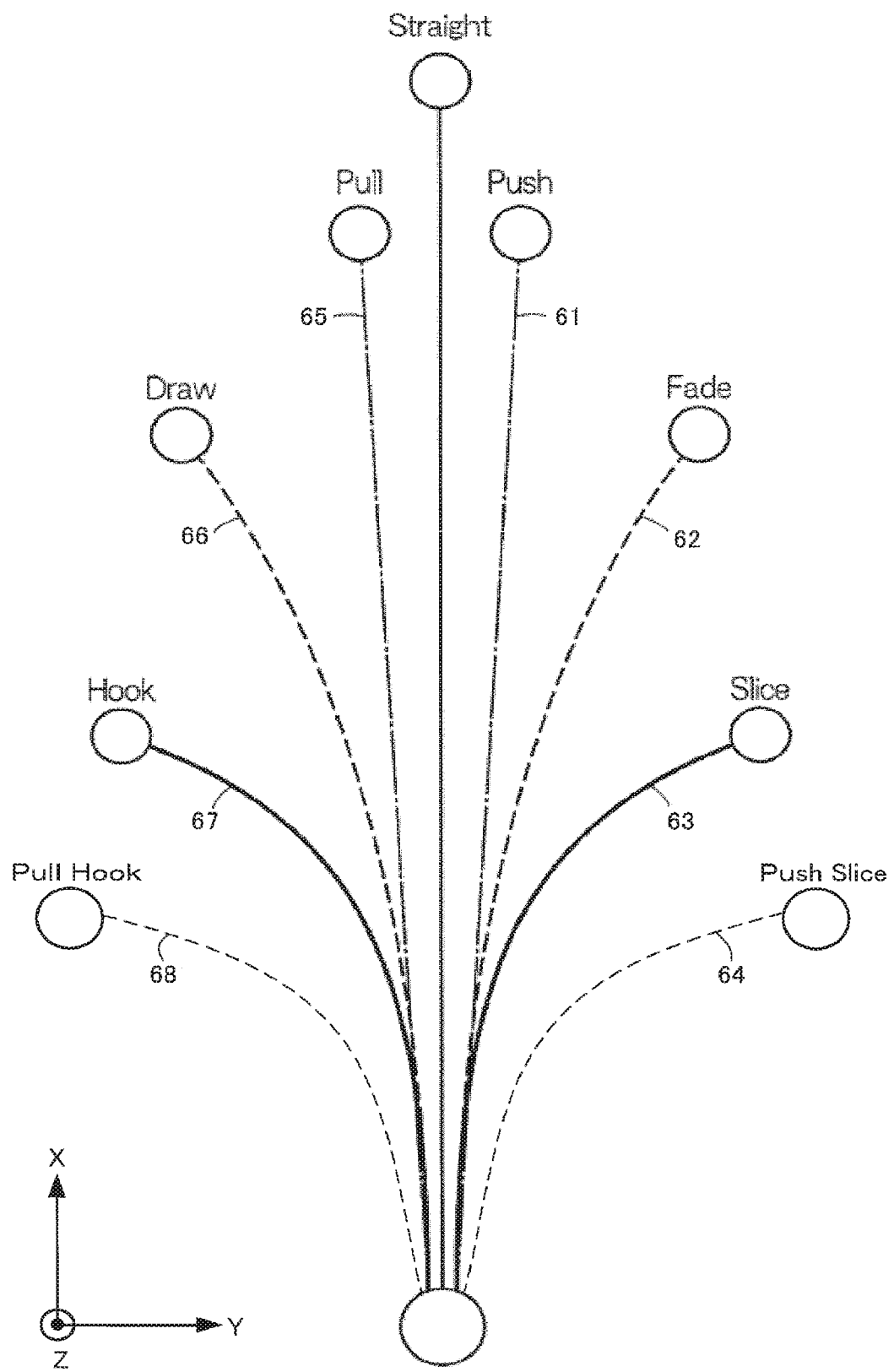
FIG. 16 is a diagram illustrating a difference in a type of projectile line.

FIG. 16 is a diagram illustrating a relation among the types of projectile lines. In FIG. 16, a relation when viewed from a right-handed user is illustrated and individual projectile line curves are roughly drawn to clarify differences between the types of projectile lines.

In FIG. 16, the type of projectile line denoted by reference numeral 61 is an example of a projectile line curve belonging to the push. The type of projectile line denoted by reference numeral 62 is an example of a projectile line curve belonging to the fade. The type of projectile line denoted by reference numeral 63 is an example of a projectile line curve belonging to the slice. The type of projectile line denoted by reference numeral 64 is an example of a projectile line curve belonging to the push slice. The type of projectile line denoted by reference numeral 65 is an example of a projectile line curve belonging to the pull. The type of projectile line denoted by reference numeral 66 is an example of a projectile line curve belonging to the draw. The type of projectile line denoted by reference numeral 67 is an example of a projectile line curve belonging to the hook. The type of projectile line denoted by reference numeral 68 is an example of a projectile line curve belonging to the pull hook.

The processing unit 21 may cause the display unit 25 to display the examples of the projectile line curves illustrated in FIG. 16, as necessary.

1-4. Advantages

As described above, the processing unit 21 according to the embodiment calculates the index θ of the movement direction of the face surface at the time of entering an impact and the index ϕ' of the posture of the face surface at the impact in order to predict the type of projectile line of the user.

Of the indexes, the index θ of the movement direction is calculated using the target line as a criterion and the index ϕ' of the posture is calculated using the movement direction of the face surface as a criterion. Therefore, a habit of the user related to the movement direction does not overlap on the index ϕ' of the posture.

Accordingly, the indexes ϕ' and θ calculated in the embodiment are considered as mutually independent amounts.

Accordingly, in the embodiment, the user can accurately comprehend his or her tendency of the projectile line based on the indexes ϕ' and θ. The processing unit 21 according to the embodiment can predict the type of projectile line of the user based on the indexes ϕ' and θ with high precision.

Since the processing unit 21 according to the embodiment displays the combination of the indexes ϕ' and θ as the two-dimensional graph or the like, the user can recognize his or her type of projectile line as coordinates of the graph.

Since the processing unit 21 according to the embodiment displays the projectile line prediction map as the background of the two-dimensional graph, the user can intuitively recognize his or her type of projectile line.

2. Modification Examples

The invention is not limited to the embodiments, but may be modified in various forms within the scope of the gist of the invention.

For example, when the golf club 3 is a right-handed golf club, the processing unit 21 may set the axial direction of the graph so that the arrangement pattern of the areas A1 to A9 is the same as that illustrated in FIG. 15. When the golf club 3 is a left-handed golf club, the processing unit 21 may set the axis direction of the graph so that the area A1 of the push slice and the area A9 of the pull hook are exchanged with each other, the area A2 of the slice and the area A8 of the hook are exchanged with each other, the area A3 of the fade and the area A7 of the draw are exchanged with each other, and the area A4 of the push and the area A6 of the pull are exchanged with each other in FIG. 15.

The processing unit 21 can determine whether the golf club 3 is a right-handed golf club or a left-handed golf club, for example, based on the club specification information 242 or the like.

When the golf club 3 is either a right-handed golf club or a left-handed golf club, the processing unit 21 preferably sets the origin of the graph such that the area A5 of the straight is located in the middle of the graph.

The processing unit 21 according to the foregoing embodiment has classified into the 9 types of projectile lines, but may classify 2 to 8 types of projectile lines or 10 or more types of projectile lines. For example, the projectile lines may be classified into 3 types of projectile lines, "hook", "straight", and "slice" or may be classified into 3 types of projectile lines, "push", "straight", and "pull". For example, when projectile lines are classified into 3 types, the above-described projectile line prediction map may be divided into 3 areas along one coordinate axis.

In the foregoing embodiment, the data reported to the user has been configured as the combination of the incident angle θ and the relative face angle ϕ'. However, the data may be configured as only the incident angle θ or may be configured as only the relative face angle ϕ'.

Figure 17:
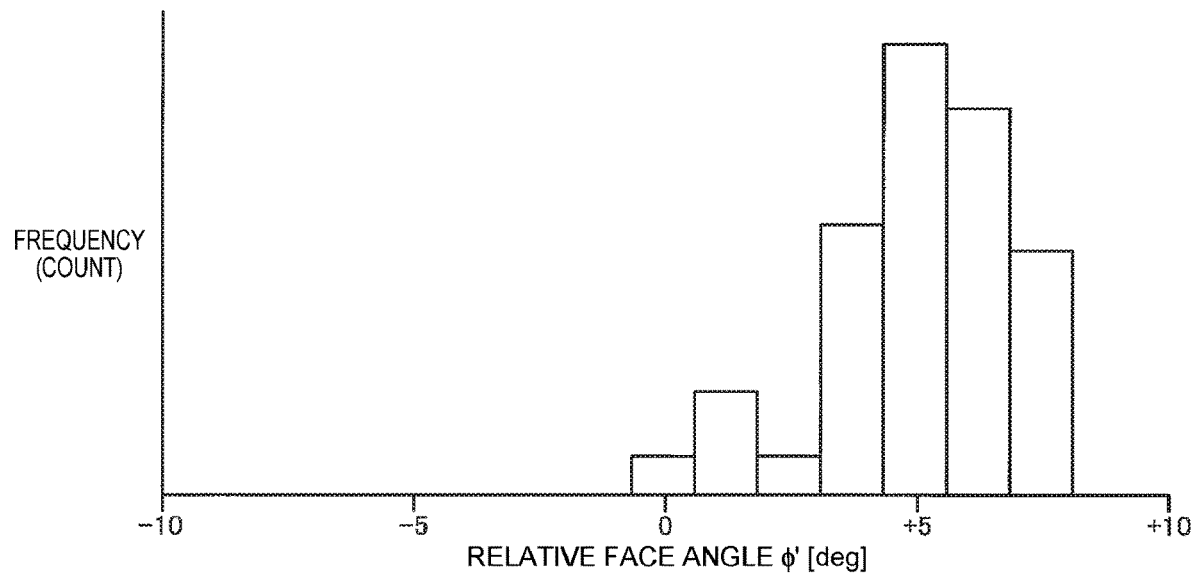
FIG. 17 is a diagram illustrating an example of a histogram of the relative face angle $\phi'$.

The processing unit 21 according to the foregoing embodiment has plotted the measurement results of the plurality of times of the user on the graph. However, the measurement results of the plurality of times of the user may be statistically calculated and the statistical results may be reported to the user. For example, as illustrated in FIG. 17, a histogram of the relative face angle ϕ' may be generated and displayed on the display unit 25. The horizontal axis of the histogram in FIG. 17 is the relative face angle ϕ' and the vertical axis of the histogram is a frequency.

The processing unit 21 according to the foregoing embodiment may generate and display a histogram of the incident angle θ as in the histogram of the relative face angle φ'.

The processing unit 21 according to the foregoing embodiment sets, as the movement direction vector $V_d(t_3)$, the unit vector oriented in the same direction as the vector in which the face coordinates $P_F(t_3)$ at time $t_3$ are a starting point and the face coordinates $P_F(t_3+\Delta t)$ at time $(t_3+\Delta t)$ are an ending point. A unit vector oriented in the same direction as a vector in which face coordinates $P_F(t_3+\Delta t)$ at time $(t_3+\Delta t)$ are a starting point and the face coordinates $P_F(t_3)$ at time $t_3$ are an ending point may be set as the movement direction vector $V_d(t_3)$.

Alternatively, a unit vector oriented in the same direction as a vector in which the face coordinates $P_F(t_3-\Delta t)$ at time $(t_3-\Delta t)$ are a starting point and the face coordinates $P_F(t_3+\Delta t)$ at time $(t_3+\Delta t)$ are an ending point may be set as the movement direction vector $V_d(t_3)$.

Alternatively, the processing unit 21 according to the foregoing embodiment may calculate the movement direction vector $V_d(t_3)$ in accordance with, for example, the following processes (1) to (3).

(1) The trajectory Q of the face coordinates $P_F$ during a given period including times before and after time $t_3$ is calculated.

(2) A tangential line of the trajectory Q at time $t_3$ is calculated.

(3) A unit vector oriented in the same direction as the tangential line is set as the movement direction vector $V_d(t_3)$.

The processing unit 21 according to the foregoing embodiment has displayed the measurement results as the graph, but may display the measurement results as numerical values.

When the processing unit 21 according to the foregoing embodiment calculates the angle formed by the movement direction vector and the face vector, the vectors have been projected to the XY plane (which is an example of the predetermined plane), but a plane to which the vectors are projected may be another predetermined plane intersecting in the vertical direction (the Z direction). For example, the plane may be a predetermined plane including a movement direction of the head (or the face surface) of the golf club.

The processing unit 21 according to the foregoing embodiment has calculated the angle formed by the movement direction vector and the face vector on the predetermined plane as the index indicating the posture of the face surface for which the movement direction of the face surface is set as the criterion. However, an angle (or the magnitude of the angle) formed by the movement direction vector and the face vector in a space (XYZ space) may be calculated.

When the processing unit 21 according to the foregoing embodiment calculates the angle formed by the movement direction vector and the face vector, the vectors have been projected to the common predetermined plane. However, the vectors may be projected to mutually different predetermined planes or only one of the vectors may be projected to a predetermined plane.

The processing unit 21 according to the foregoing embodiment has used the angle between the movement direction vector and the face vector as the index indicating the posture of the face surface for which the movement direction of the face surface is set as the criterion. However, for example, another index such as a difference vector between the movement direction vector and the face vector may be used.

The processing unit 21 according to the foregoing embodiment has used the unit vector (which is an example of a predetermined vector intersecting a ball hitting surface) oriented in the +X axis direction at time $t_0$ as the face vector. However, another vector fixed to the face surface may be used as the face vector. For example, a unit vector (which is an example of a predetermined vector which lies along the ball hitting surface) oriented in the −Y axis direction at time to may be used as the face vector.

Alternatively, when the posture of the face surface at time $t_0$ is known from the club specification information 242 and the sensor-mounted position information 244, a normal vector (which is an example of a predetermined vector intersecting the ball hitting surface) of the face surface may be used as the face vector.

The processing unit 21 according to the foregoing embodiment has displayed the measurement result as the graph, but may directly display the type of projectile line predicted from the measurement result instead of the display of the graph or in addition to the display of the graph. In this case, for example, the processing unit 21 may display a text image indicating the predicted type of projectile line on the display unit 25 or may display an image of a projectile line curve indicating the predicted type of projectile line on the display unit 25.

The processing unit 21 according to the foregoing embodiment has adopted the image as the report form of the measurement result. However, for example, another report form such as a time change pattern of light intensity, a time change pattern of a color, a change pattern of sound strength, a change pattern of a sound frequency, or a rhythm pattern of vibration may be adopted.

In the foregoing embodiment, some or all of the functions of the processing unit 21 may be mounted on the side of the sensor unit 10. Some of the functions of the sensor unit 10 may be mounted on the side of the processing unit 21.

In the foregoing embodiment, some or all of the processes of the processing unit 21 may be executed by an external device (a tablet PC, a note PC, a desktop PC, a smartphone, a network server, or the like) of the swing analysis device 20.

In the foregoing embodiment, some or all of the acquired data may be transmitted (uploaded) to an external device such as a network server by the swing analysis device 20. The user may browse or download the uploaded data with the swing analysis device 20 or an external device (a personal computer, a smartphone, or the like), as necessary.

The swing analysis device 20 may be another portable information device such as a head mount display (HMD) or a smartphone.

In the foregoing embodiment, the sensor unit 10 is mounted on the grip of the golf club 3, but may be mounted on another portion of the golf club 3.

In the foregoing embodiment, each motion of a swing of the user 2 has been detected using the square root of the sum of the squares as in formula (1) as the composite value of the triaxial angular velocity measured by the sensor unit 10. Alternatively, a sum of squares of the triaxial angular velocities, a sum or an average value of the triaxial angular velocities, a product of the triaxial angular velocities, or the like may be used as the composite value of the triaxial angular velocities. Instead of the composite value of the triaxial angular velocities, a composite value of triaxial accelerations such as a sum or a square root of squares of the triaxial accelerations, a sum or an average value of the triaxial acceleration, or a product of the triaxial accelerations may be used.

In the foregoing embodiment, the acceleration sensor 12 and the angular velocity sensor 14 are embedded to be integrated in the sensor unit 10. However, the acceleration sensor 12 and the angular velocity sensor 14 may not be integrated. Alternatively, the acceleration sensor 12 and the angular velocity sensor 14 may be mounted directly on the golf club 3 or the user 2 without being embedded in the sensor unit 10. In the foregoing embodiment, the sensor unit 10 and the swing analysis device 20 are separated from each other. However, the sensor unit 10 and the swing analysis device 20 may be integrated to be mounted on the golf club 3 or the user 2.

In the foregoing embodiment, the swing analysis system (swing analysis device) analyzing a gold swing has been exemplified. However, the invention can be applied to a swing analysis system (swing analysis device) analyzing swings of various exercises such as tennis or baseball.

The foregoing embodiments and modification examples are merely examples, but the invention is not limited thereto. For example, the embodiments and the modification examples can also be appropriately combined.

The invention includes configurations (for example, configurations in which functions, methods, and results are the same or configurations in which objects and advantages are the same) which are substantially the same as the configurations described in the embodiments. The invention includes configurations in which non-essential portions of the configurations described in the embodiments are substituted. The invention includes configurations in which the same operational advantages as the configurations described in the embodiments are obtained or configurations in which the same objects can be achieved. The invention includes configurations in which known technologies are added to the configurations described in the embodiments.

The entire disclosure of Japanese Patent Application No. 2014-258533, filed Dec. 22, 2014 is expressly incorporated by reference herein.

What is claimed is:

1. A motion analysis system comprising:
   a wireless inertial sensor that is configured to attach to a shaft of a golf club, and that measures acceleration; and
   a processor that is configured to wirelessly communicate with the wireless inertial sensor, and that is programmed to:
      calculate, based on measured acceleration data received from the wireless inertial sensor, an initial position and an initial posture of a ball hitting surface of the golf club at a timing of starting a swing;
      detect, based on the received measured acceleration data, a timing of actual impact between the ball hitting surface of the golf club and a golf ball;
      calculate a movement direction of the ball hitting surface of the golf club and an impact posture of the ball hitting surface at the timing of actual impact;
      calculate a relative angle of the ball hitting surface of the golf club at the timing of actual impact based on the calculated movement direction and the calculated impact posture of the ball hitting surface at the timing of actual impact; and
      cause a display to display
   projection-related data based on the calculated relative angle of the ball hitting surface at the timing of actual impact.

2. The motion analysis system according to claim 1, wherein the processor is further programmed to: obtain a face vector indicating the initial posture of the ball hitting surface at the timing of starting the swing based on the measured acceleration data received from the wireless inertial sensor.

3. The motion analysis system according to claim 1, wherein the processor is further programmed to: calculate a movement direction vector of the ball hitting surface at the timing of starting the swing based on the calculated impact posture of the ball hitting surface at the timing of actual impact.

4. The motion analysis system according to claim 3, wherein the movement direction vector of the ball hitting surface at the timing of starting the swing is projected on a predetermined plane intersecting the ball hitting surface in a vertical direction.

5. The motion analysis system according to claim 1, wherein the displayed projection-related data includes: a swing path and relative rotation angle.

6. The motion analysis system according to claim 1, wherein the processor is further programmed to: calculate a movement direction of the ball hitting surface at the timing of actual impact.

7. The motion analysis system according to claim 1, wherein the processor is further programmed to: calculate, as the relative face angle of the ball hitting surface at the timing of actual impact, an angle formed by a movement direction vector and a face vector on an XY plane.

8. The motion analysis system according to claim 1, wherein the processor is further programmed to control the display to display, as the projection-related data, a type of predicted projectile line.

9. The motion analysis system according to claim 8, wherein the processor is further programmed to control the display to display a map including an area that is divided in accordance with the type of projectile line, and a two-dimensional graph.

10. The motion analysis system according to claim 9, wherein the processor is further programmed to control the display to display the predicted projectile line in the middle of the two-dimensional graph.

11. The motion analysis system according to claim 1, wherein the processor is further programmed to control the display to display a plurality of pieces of data regarding a plurality of swings at a plurality of times with a two-dimensional graph and to distinguish recent data from other data that is not recent on the two-dimensional graph.

12. The motion analysis method according to claim 1, wherein the processor is further programmed to: cause the display to display, as the projection-related data, the movement direction vector of the ball hitting surface at the timing of starting the swing on a predetermined plane intersecting the ball hitting surface in a vertical direction.

13. A motion analysis method comprising:
   calculating, based on measured acceleration data received from a wireless inertial sensor, an initial position and an initial posture of a ball hitting surface of the golf club at a timing of starting a swing, the wireless inertial sensor being configured to attach to a shaft of a golf club, and to measure acceleration;
   detecting, based on the received measured acceleration data, a timing of actual impact between the ball hitting surface of the golf club and a golf ball;
   calculating a movement direction of the ball hitting surface of the golf club and an impact posture of the ball hitting surface at the timing of actual impact;
   calculating a relative angle of the ball hitting surface of the golf club at the timing of actual impact based on the calculated movement direction and the calculated impact posture of the ball hitting surface at the timing of actual impact; and causing a display to display projection-related data based on the calculated relative angle of the ball hitting surface at the timing of actual impact.

14. A non-transitory computer readable medium that stores motion analysis program instructions that, when executed by a computer, causes the computer to:

calculate, based on measured acceleration data received from a wireless inertial sensor, an initial position and an initial posture of a ball hitting surface of the golf club at a timing of starting a swing, the wireless inertial sensor being configured to attach to a shaft of a golf club, and to measure acceleration;

detect, based on the received measured acceleration data, a timing of actual impact between the ball hitting surface of the golf club and a golf ball;

calculate a movement direction of the ball hitting surface of the golf club and an impact posture of the ball hitting surface at the timing of actual impact;

calculate a relative angle of the ball hitting surface of the golf club at the timing of actual impact based on the calculated movement direction and the calculated impact posture of the ball hitting surface at the timing of actual impact; and cause a display to display projection-related data based on the calculated relative angle of the ball hitting surface at the timing of actual impact.

* * * * *